United States Patent [19]

Haynes et al.

[11] Patent Number: 5,156,611

[45] Date of Patent: Oct. 20, 1992

[54] BLOOD MICROSAMPLING SITE PREPARATION METHOD

[75] Inventors: John L. Haynes, Chapel Hill; George R. Titus, Raleigh, both of N.C.

[73] Assignee: Becton, Dickinson and Company, Franklin Lakes, N.J.

[21] Appl. No.: 474,877

[22] Filed: Feb. 5, 1990

[51] Int. Cl.⁵ ............................................. A61B 17/32
[52] U.S. Cl. ................................................... 606/181
[58] Field of Search ............................... 128/760, 764; 606/181–183

[56] References Cited

U.S. PATENT DOCUMENTS

| | | |
|---|---|---|
| 3,367,332 | 2/1968 | Groves . |
| 3,741,197 | 6/1973 | Sanz et al. ............................ 606/182 |
| 4,089,331 | 5/1978 | Hartigan et al. . |
| 4,374,126 | 2/1983 | Cardarelli et al. ..................... 424/81 |
| 4,434,181 | 2/1984 | Marks, Sr. et al. ................... 424/326 |
| 4,483,759 | 11/1984 | Szycher et al. .................. 204/159.24 |
| 4,542,012 | 9/1985 | Dell ........................................ 424/28 |
| 4,589,421 | 5/1986 | Ullman ................................. 128/763 |
| 4,613,544 | 9/1986 | Burleigh .......................... 428/315.5 |
| 5,014,718 | 5/1991 | Mitchen ................................ 606/181 |

FOREIGN PATENT DOCUMENTS 2909349  9/1980  Fed. Rep. of Germany ...... 606/181

*Primary Examiner*—Max Hindenburg
*Attorney, Agent, or Firm*—Richard E. Brown; Nanette S. Thomas

[57] ABSTRACT

A method for collecting blood while preserving the integrity of the blood sample is provided. The method includes the steps of applying a protective layer to the skin, lancing the skin through the protective layer, allowing blood from the subject to accumulate on the protective layer, and collecting a sample of the blood accumulated on the protective layer. The protective layer may be formed in situ or applied as a tape. In either case, the surface of the protective layer should be hydrophobic.

15 Claims, No Drawings

BLOOD MICROSAMPLING SITE PREPARATION METHOD

SUMMARY OF THE INVENTION

The field of the invention relates to the sampling of blood through the techniques of lancing the skin and collecting blood through the use of a capillary tube or other collection device.

Blood samples are generally obtained through the use of syringes when relatively large samples are required. Smaller samples may be obtained by simply lancing a finger or other part of a subject's body, waiting for a blood drop to form, and moving the end of a capillary tube into contact with the drop. Blood is collected by means of capillary action. U.S. Pat. No. 4,589,421 discloses a method for performing the latter technique.

Blood samples obtained from lanced skin sites are likely to be contaminated with skin oils and bacteria even if the sites are first washed. There may also be triggering of platelets in the blood upon skin contact. In addition, the blood often tends to spread out over the skin, making it more difficult to obtain a sample and increasing the likelihood of the blood contacting the phlebotomist.

SUMMARY OF THE INVENTION

It is an object of the invention to provide a method for sampling blood from a subject which avoids a number of problems ordinarily encountered when obtaining blood from lanced skin sites.

It is another object of the invention to provide a method for sampling blood which provides a better quality blood sample than when using conventional techniques.

A still further object of the invention is to facilitate the sampling of blood from lanced skin sites.

In accordance with these and other objects of the invention, a method is provided which includes the steps of applying a protective layer to the skin of a subject, lancing the skin through the protective layer, allowing blood from the subject to accumulate on the protective layer, and collecting a sample of the blood accumulated on the protective layer.

The protective layer is preferably formed in situ from a liquid preparation, a gel or other substance which can be applied to the skin. In the case of a liquid, a polymer or other material may be contained within a volatile solvent, such as alcohol, which will leave a thin film layer upon the skin upon evaporation of the solvent. Other liquids containing no solvent can be employed providing they dry after a reasonable time upon contact with air and are removable once the blood sample is collected. If an oil or grease is used to form the protective film, drying is unnecessary due to their hydrophobicity.

The blood sample may be taken by means of a capillary tube. By using a protective film which is non-wetting, the blood is easier to pick up than if it is allowed to spread over the skin. The integrity of the blood sample is maintained by using this procedure as it never contacts the subject's skin.

DETAILED DESCRIPTION OF THE INVENTION

The invention provides a method for preserving the integrity of a blood sample obtained from a subject through an opening in the skin.

A thin, protective film is first applied to the subject's skin on the area which the phlebotomist intends to lance. As will be described hereafter, the film may be applied as a liquid, a gel or in other form wherein a thin film will remain upon the skin on or shortly after application. The film is preferably hydrophobic.

Next, the skin protected by the film is lanced with a lancet or any other suitable medical instrument designed for cutting or piercing the skin. Only a small incision is desirable or necessary.

Once the skin is pierced, blood flows through the incision and collects upon the protective film. The film should be applied over a sufficient area that the blood does not contact the skin. The skin is preferably lanced near the center of the area covered by the film to insure the blood contacts nothing but the film.

As the blood collects upon the film, it will tend to form as a drop due to cohesion. The film, being substantially non-wetting, discourages the spreading of the drop about the lanced site. The film should also be non-thrombogenic.

Once a sufficient amount of blood has accumulated about the lanced site, it may be collected by the phlebotomist. One common method of collecting blood is to contact the blood with the end of a capillary tube and allow the tube to fill by capillary action. Another method is to allow the blood to drip into a container which can be used for storage and/or analysis.

By employing a hydrophobic film in accordance with the invention, the blood is easier to collect as it does not tend to spread upon the subject's skin. More blood is available for collection by using the above techniques as it does not adhere to the film as it does to skin. Larger samples are accordingly available for the laboratory. The method according to the invention is also more aseptic than the conventional procedure, the film protecting both the patient and the blood sample.

In accordance with a preferred embodiment of the invention, the protective film is formed in situ. This can be accomplished in a number of different ways. One approach is to provide a polymer dissolved within a volatile solvent, such as an acrylate within alcohol. Upon evaporation of the alcohol, a thin, hydrophobic film remains on the skin. The film is easily washed away by using the same type of solvent in which it was originally dissolved. Acrylates, alkyl acrylates, or other polymers such as aliphatic polyesters dissolved in acetone, or ethylene vinyl acetate in freon may also be employed, though they are not preferred. Other possible materials for use as the protective layer are nitrocellulose and soluble cellulose derivatives.

A second method for forming a thin protective film is by in situ polymerization. A liquid or gelatinous formulation containing acrylate monomers or oligomers is smeared over the area of interest into a thin film. Exposure to air triggers a polymerization reaction of the residual acrylates forming a thin, solid hydrophobic film. Once the skin is pierced through the film and blood collected, the film may be peeled away or removed with a solvent.

A monomer having the general formula shown below may be used for in situ polymerization on a subject's skin:

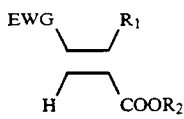

where EWG is an electron withdrawing group such as CN or $NO_2$, $R_1$ is an alkyl or hydrogen, and $R_2$ is an alkyl or alkenyl ($C_1$–$C_{18}$) or other homolog. The hydrophobic nature and physio-mechanical properties of the polymers used are controlled by variations in $R_1$ and $R_2$. For example, hydrophobicity will increase as the chain lengths of these groups increase. The formulation applied to the skin for in situ polymerization is applied in the absence of a solvent.

A less preferred method of providing in situ polymerization is through the use of activated acrylates wherein the activation mechanism is infrared light.

The use of an aerosol to provide a quick drying polymer film on the surface of the skin is another method through which the objects of the invention may be accomplished. Liquid or gelatinous applications are, however, preferred for phlebotomy.

A third method of applying a film in accordance with the invention is to use an oil or grease containing preparation to provide the desired non-wetting surface surrounding the intended wound site. Many of the greases or oils used as bases for topical medications can be employed for this purpose. Petroleum jelly is one such material which can be employed as a protective, hydrophobic film. The material applied to the skin would not be required to dry or solidify before the skin is lanced, unlike the two methods discussed above.

In addition to providing a hydrophobic surface which facilitates the collection of blood while maintaining the integrity of the blood sample, the protective film may be formulated to provide other properties as well. The use of alcohol as a solvent provides a disinfectant in the area which is to be lanced. An anticoagulant such as Heparin and an anesthetic such as Lidocaine may also be incorporated within the film material.

If the puncture site is pre-warmed, blood flow will be increased, thereby facilitating the collection procedure. Such warming can be accomplished by providing in situ exothermic polymerization, as described above.

As an alternative to the in situ film formation as described above, the protective layer applied to the skin may be in the form of a patch or tape. A tape, for example, is adhered to the skin pric to the lancing operation. Upon lancing, the blood flows through the skin and lanced opening in the tape. The blood is collected as it accumulates upon the outer surface of the tape.

It is important that the tape be non-absorbent and hydrophobic in all areas where it would be contacted by blood. It is also important that the tape be positioned in close, adjoining position to the skin so that the blood tends to accumulate on the outer surface of the tape and not beneath it. Alcohol may be wiped upon the outer surface of the tape to insure it is free from contaminants.

The patch or tape used in accordance with the invention may be made from any suitable material, and preferably an inert, pliable polymeric film material having a thickness not exceeding several mils. Polyethylene, polyvinylchloride and other non-absorptive films can be employed. An adhesive may be provided on the layer which contacts the skin to insure proper blood flow through the film.

Although illustrative embodiments of the present invention have been described herein, it is to be understood that the invention is not limited to those precise embodiments, and that various other changes and modifications may be effected therein by one skilled in the art without departing from the scope or spirit of the invention.

What is claimed is:

1. A method of collecting a blood sample from a subject comprising the steps of:
   applying an in-situ formed protective layer to the skin of a subject;
   lancing a portion of the skin through the protective layer;
   allowing blood from the lanced portion of the skin to accumulate on a surface of said protective layer; and
   collecting a sample of said blood accumulated on said protective layer.

2. A method as defined in claim 1 wherein said protective layer comprises at least one polymer that is applied to the skin by means of a volatile solvent.

3. A method as defined in claim 2 wherein said solvent is selected from the group consisting of freon, acetone or an alcohol.

4. A method as defined in claim 1 wherein said protective layer comprises at least one polymer.

5. A method as defined in claim 4 wherein said protective layer comprises a polymer that is formed after application of a reactive monomer to the skin.

6. A method as defined in claim 5 wherein said reactive monomer is acrylate.

7. A method as defined in claim 4 wherein said polymer is selected from the group consisting of ethylene vinyl acetate, an aliphatic polyester of an acrylate.

8. A method as defined in claim 4 wherein said polymer is an acrylate.

9. A method as defined in claim 4 wherein said polymer is an alkyl acrylate.

10. A method as defined in claim 5 wherein said polymerization reaction is activated by moisture, oxygen or infrared radiation.

11. A method as defined in claim 1 wherein said protective layer comprises an oil.

12. A method as defined in claim 1 wherein said protective layer comprises grease.

13. A method as defined in claim 1 including the step of contacting said blood accumulated on said protective layer with an end of a capillary tube.

14. A method as defined in claim 1 wherein said protective layer includes an anticoagulant.

15. A method as defined in claim 1 wherein said protective layer forms a hydrophobic surface upon said skin.

* * * * *